United States Patent [19]

Te-Wei et al.

[11] Patent Number: 5,210,270

[45] Date of Patent: May 11, 1993

[54] METHOD FOR SYNTHESIS AND $^{99m}$C LABELLING OF 2-ALKOXYISOBUTYLISONITRILE

[75] Inventors: Lee Te-Wei; Ting Gann, both of Taipei; Su Chang-Shinn; Chyi Shyh-Yi, both of Tau-Yen, all of Taiwan

[73] Assignee: Institute of Nuclear Energy Research, Taiwan

[21] Appl. No.: 797,066

[22] Filed: Nov. 25, 1991

[51] Int. Cl.$^5$ ............................................ C07C 249/00
[52] U.S. Cl. ........................................ 558/302; 534/14
[58] Field of Search ........................................ 558/302

[56] References Cited

U.S. PATENT DOCUMENTS

| | | | |
|---|---|---|---|
| 3,197,493 | 7/1965 | Allison | 558/302 X |
| 3,539,606 | 11/1970 | Murdoch et al. | 558/302 X |
| 4,303,786 | 12/1981 | Goldstein et al. | 558/302 X |
| 4,452,774 | 6/1984 | Jones et al. | 558/302 X |
| 4,707,544 | 11/1987 | Jones et al. | 558/302 X |
| 4,735,793 | 4/1988 | Jones et al. | 558/302 X |
| 4,834,909 | 5/1989 | Nagel | 558/302 X |
| 4,864,051 | 9/1989 | Ramalingham | 558/302 |
| 4,885,100 | 12/1989 | Igbal et al. | 558/302 X |
| 4,988,827 | 1/1991 | Bergstein et al. | 558/302 X |

*Primary Examiner*—Joseph Paul Brust
*Attorney, Agent, or Firm*—Burns, Doane, Swecker & Mathis

[57] ABSTRACT

A new method for synthesizing 2-alkoxyisobutylisonitrile is provided in which isobutylene is used as the starting material. The haloalkoxylation of isobutylene in alcohol medium gives 2-alkoxyisobutylhalide which is then converted to 2-alkoxyisobutylamine. In the basic condition, the reaction of 2-alkoxyisobutylamine with chloroform produces 2-alkoxyisobutylisonitrile. The synthesis process contains three steps by which a higher yield is achieved. 2-Alkoxyisobutylisonitrile is labelled with technetium-99m by exchange labelling of stable tetrakis(2-alkoxyisobutylisonitrile)copper(I) complex. Tetrakis(2-alkoxyisobutylisonitrile)copper(I) complex can be prepared by the exchange of acetonitrile molecules in tetrakis(acetonitrile)copper(I) complex with isonitrile ligands.

7 Claims, No Drawings

METHOD FOR SYNTHESIS AND $^{99m}$C LABELLING OF 2-ALKOXYISOBUTYLISONITRILE

FIELD OF THE INVENTION

This invention relates to a novel synthesis of 2-alkoxyisobutylisonitrile, copper isonitrile adducts and radioactive isotope labelling such as $^{99m}$Tc.

BACKGROUND OF THE INVENTION $^{99m}$Tc labelling isonitrile compounds have been proven to be myocardial perfusion agents. The synthesis of ether isonitrile ligands has been described by Bergstein et al in European Pat. 233368 issued Oct. 26, 1987. The most useful of ether isonitrile compound is 2-methoxyisobutylisonitrile, synthesis of which is described by Bergstein as follows:

SUMMARY OF THE INVENTION

The main object of the present invention is to provide a new method for synthesis and $^{99m}$Tc labelling of 2-alkoxyisobutylisonitrile. Isobutylene is haloalkoxylated with N-halosuccinimide in the presence of alcohol solution to give 2-alkoxyisobutylhalide. This is followed by reaction of potassium phthalimide with 2-alkoxyisobutylhalide, following by hydrazinolysis with hydrazine to yield 2-alkoxyisobutylamine. Finally, in the basic condition, the reaction of 2-alkoxyisobutylamine with chloroform in the presence of catalyst benzyltriethylammonium chloride produces 2-alkoxyisobutylisonitrile.

The new synthesis method of these isonitriles has also

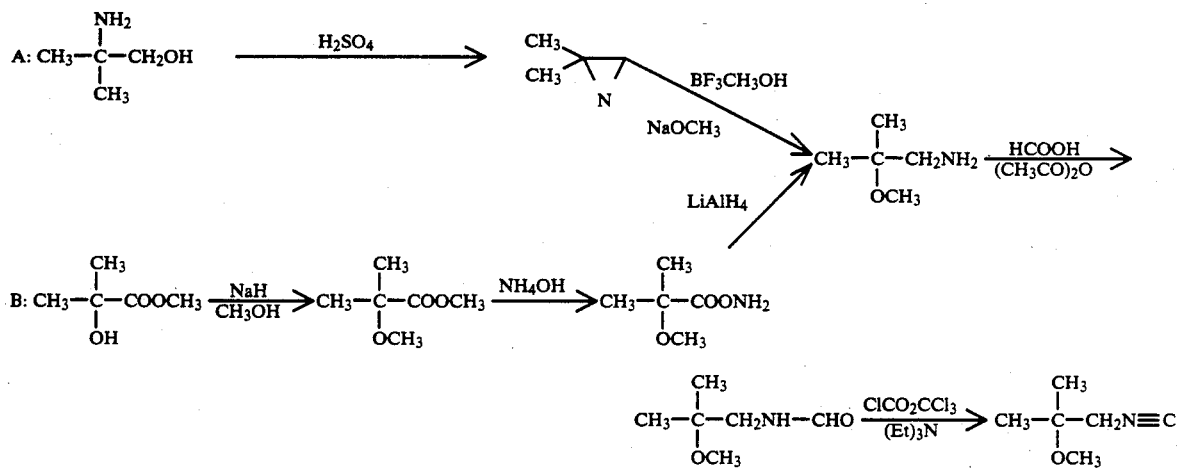

In both of the above (A) and (B) synthetic routes, which include 4 and 5 steps respectively, the total yield is only 5.9–8.1%. Van Wyk et al. developed a method to synthesize both 2-methoxyisobutylisonitrile and 2-ethoxyisobutylisonitrile, which was published under the title "Synthesis and $^{99m}$Tc Labelling of MMI(MIBI) and its Ethyl Analogue EMI", Appl. Radiat. Isot. 1991, 42:687

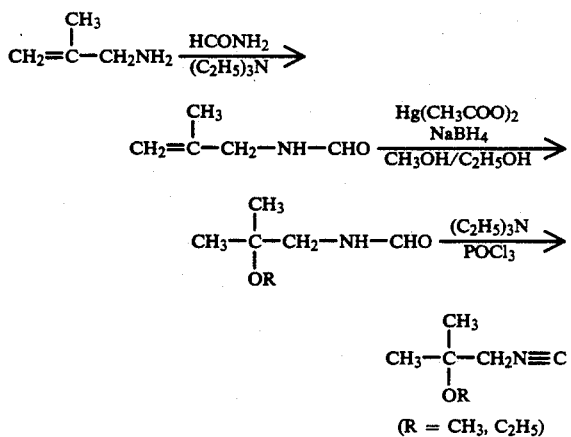

(R = CH$_3$, C$_2$H$_5$)

The possible contamination of mercury on the product is a disadvantage of the above process. There is a question of whether or not mercury acetate reagent proved to be more clean, more efficient and convenient than known methods in the literature.

The $^{99m}$Tc labelling of 2-alkoxyisobutylisonitrile is performed by mixing copper isonitrile adducts with radioactive isotope $^{99m}$Tc. Such an adduct is labelled easily and rapidly with $^{99m}$Tc and produces good yields. Tetrakis(2-alkoxyisobutylisonitrile)copper(I)tetrafluoroborates can be prepared by the exchange of acetonitrile molecules in tetrakis(acetonitrile) copper(I)tetrafluoroborate with 2-alkoxyisobutylisonitrile ligand at room temperature.

DETAILED DESCRIPTION OF THE INVENTION

The haloalkoxylation of alkenes can be achieved by halogen in alcohol as shown in equation(1).

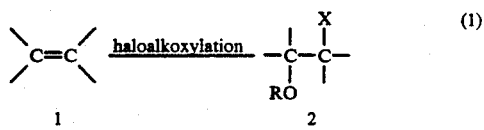

This procedure provides a convenient and high yields 2 from olefins. Reaction of potassium phthalimide with 2 leads to the N-alkylphthalimide. N-Substituted phthalimides may be converted into the corresponding 3 by hydrolysis or hydrazinolysis. Synthesis of 3 may be summarized schematically as equation(2).

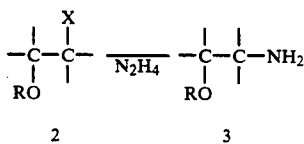

(2)

It is obvious that 3 formed in this reaction will be uncontaminated by secondary or tertiary amines. The phase-transfer catalysis method has been utilized effectively for synthesis of isonitriles.

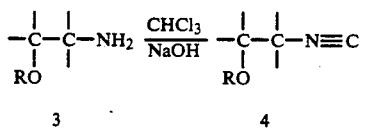

(3)

The reaction between 3 and chloroform in NaOH solution and catalyst benzyltriethylammonium chloride gives 4 as shown in equaiton(3). This invention can be further described by the following examples in which the percentages are expressed by weight unless otherwise indicated.

EXAMPLE 1

Synthesis of 2-methoxyisobutylbromide

N-Bromosuccinimide (3.56 g, 0.02 mol) was dissolved in methanol. The solution was cooled to $-10°$ C. in an ice/acetone bath. Isobutylene was slowly introduced and stirred for 5 hours and poured into separatory funnel containing saturated NaCl water. The organic layer was removed and aqueous layer was extracted with three 100 ml portions of dichloromethane. The combined organic extractants was dried over anhydrous magnesium sulfate and filtered, and the solvent was mostly removed by rotary evaporatory. The resulting solution was distilled at atmospheric pressure and the product collected at 140° C. (3.14 g, 94% yield).

IR(neat/$\nu$ cm$^{-1}$): 2960, 2920, 2820, 1450, 1415, 1370, 1360, 1090, 1065, 735, 660

$^1$HNMR(200MHz, CDCl$_3$/$\delta$ ppm): 1.30(s,6H,2CH$_3$), 3.24(s, 3H, OCH$_3$), 3.41(s, 2H, CH$_2$)

$^{13}$CNMR(200MHz, CDCl$_3$/$\delta$ ppm): 23.71(s, 2CH$_3$) 40.91(s, CH$_2$), 49.79(s, OCH$_3$),

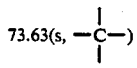

73.63(s, —C—)

I EXAMPLE 2

Synthesis of 2-methoxyisobutyliodide

N-Iodosuccinimide(4.50 g, 0.02 mol) was dissolved in methanol. This was cooled to $-15°$ C. in an ice/acetone bath. Isobutylene was slowly introduced and stirred for 4 hours and poured into separatory funnel containing saturated NaCl water. The organic layer was removed and aqueous layer was extracted with three 100 ml portions of dichloromethane. The combined organic extractants was dried over anhydrous magnesium sulfate and filtered, and the solvent was mostly removed by rotary evaporatory. The resulting solution was concentrated under reduced pressure at 10 mm Hg pressure and 50° C. temperature(4.07 g, 95% yield).

IR(neat/$\nu$ cm$^{-1}$): 2980, 2950, 2840, 1470, 1420, 1380, 1365, 1095, 1070, 740, 620.

$^1$HNMR(200MHz, CDCl$_3$/$\delta$ ppm): 1.26(s,6H,2CH$_3$), 3.15(s, 3H, OCH$_3$) 3.24(s, 2H, CH$_2$)

EXAMPLE 3

Synthesis of 2-methoxyisobutylamine

Potassium phthalimide(3.70 g, 0.02 mol) was added to a solution of 2-methoxyisobutylbromide(3.34 g, 0.02 mol) in 100 ml of dimethylformamide. Stirring and reflux were continued for 4 hours, and the temperature dropped slowly to 25° C. After the addition of 200 ml of chloroform, the mixture was poured into 500 ml of cold water. The aqueous phase was separated and extracted with two 50 ml portions of chloroform. The combined chloroform extractants were washed with 100 ml of 0.2N sodium hydroxide and 100 ml of water. After drying the chloroform was removed. The residue was added to hydrazine (2 g, 0.04 mol) in 100 ml of methanol and was heated under reflux for an hour. The methanol was removed by concentration under reduced pressure. Concentrated hydrochloric acid was added to the residual aqueous solution and the mixture was heated under reflux for an hour. The solution was then concentrated under reduced pressure to remove most of the hydrochloric acid. The moist residue was adjusted pH=14 using sodium hydroxide and was poured into separatory funnel containing saturated K$_2$CO$_3$ solution. The resulting solution was distilled at atmospheric pressure and the product collected at 125° C. (1.6 g, 78% yield).

IR(neat/$\nu$ cm$^{-1}$):3280, 3065, 2960, 2920, 1640, 1430, 1365, 1075.

$^1$NHMR(200MHz, CDCl$_3$/$\delta$ ppm): 1.13(s,6H,2CH$_3$), 1.17(s, 2H, NH$_2$), 2.61 (s, 2H, CH$_2$), 3.2(s, 3H, OCH$_3$).

$^{13}$NMR(200MHz, CDCl$_3$/$\delta$ ppm): 22.54(s, 2CH$_3$), 49.39(s, CH$_2$), 50.50(s, OCH$_3$),

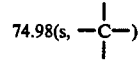

74.98(s, —C—)

EXAMPLE 4

Synthesis of 2-methoxyisobutylisonitrile

A mixture of 2-methoxyisobutylamine(2.06 g, 0.02 mol), chloroform (4,80 g, 0.04 mol) benzyltriethylammonium chloride (40 mg, 0.17 mmol) in 50 ml of dichloromethane, was added dropwise into a flask containing sodium hydroxide solution (3.2 g NaOH and 5 ml H$_2$O). The mixture solution wa heated under reflux for two hours. After the reaction mixture was diluted with 100 ml of ice water, the organic layer was separated and retained, and the aqueous layer was extracted with 50 ml of dichloromethane. The dichloromethane solutions were combined and dried over anhydrous magnesium sulfate. The resulting solution was concentrated under reduced pressure at 25 mm Hg pressure and the product collected at 55°-60° C.(1.42 g, 63% yield).

IR(neat/$\nu$ cm$^{-1}$): 2980, 2940, 2830, 2150, 1460, 1435, 1390, 1370, 1080.

$^1$HNMR(200MHz, CDCl$_3$/$\delta$ ppm): 1.28(s,6H,2CH$_3$), 3.26(s, 3H, OCH$_3$), 3.38(t, 2H, CH$_2$)

$^{13}$CNMR(200MHz, CDCl$_3$/$\delta$ ppm): 22.47(s, 2CH$_3$), 49.97(s, OCH$_3$), 50.57(t, CH$_2$), 73.34(s, —C—) 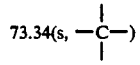

EXAMPLE 5

Synthesis of 2-ethoxyisobutylbromide

N-Bromosuccinimide (3.56 g, 0.02 mol) was dissolved in ethanol. The product was obtained by procedures analogous to those described in Example 1(95% yield).

IR(neat/$\nu$ cm$^{-1}$): 2980, 2940, 2900, 2880, 1460, 1440, 1380, 1360, 1120, 1068.

$^1$HNMR(200MHz, CDCl$_3$/$\delta$ ppm): 1.19(t,3H,CH$_3$), 1.31(s,6H,2CH$_3$), 3.44(m, 4H, CH$_2$ and OCH$_2$)

$^{13}$CNMR(200MHz, CDCl$_3$/$\delta$ ppm): 16.01(s, CH$_3$), 24.48(s,2CH$_3$), 41.23(s,CH$_2$Br),57.31(S,OCH$_2$), 73.52(s, —C—) 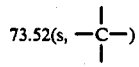

EXAMPLE 6

Synthesis of 2-ethoxyisobutylamine

The product was obtained by procedures analogous to those described in Example 3(75% yield).

IR(neat/$\nu$ cm$^{-1}$): 3380, 2980, 2950, 2850, 1660, 1470, 1430, 1398, 1370, 1120, 1075.

$^1$HNMR(200MHz, CDCl$_3$/$\delta$ ppm): 1.15(m, 11H, 2CH$_3$, CH$_3$ and NH$_2$), 2.60(s, 2H, CH$_2$), 3.38(q,2H,OCH$_2$)

$^{13}$CNMR(200MHz, CDCl$_3$/$\delta$ ppm): 16.26(s,CH$_3$), 23.25(s, 2CH$_3$), 50.92(s,CH$_2$), 56.71(s, OCH$_3$), 73.79(s, —C—) 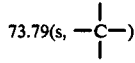

EXAMPLE 7

Synthesis of 2-ethoxyisobutylisonitrile

The product was obtained by procedures analogous to those described in Example 4 (60% yield).

IR(neat/$\nu$ cm$^{-1}$) 2980, 2930, 2900, 2870, 2150, 1475, 1450, 1385, 1360, 1120, 1070.

$^1$HNMR(200MHz, CDCl$_3$/$\delta$ ppm): 1.14(t, 3H, CH$_3$), 1.28(s, 6H, 2CH$_3$), 3.37(t, 2H, CH$_2$), 3.45(q, 2H, OCH$_2$)

$^{13}$CNMR(200MHz, CDCl$_3$/$\delta$ ppm): 15.99(s, CH$_3$), 23.22(s, 2CH$_3$), 50.89(t, CH$_2$), 57.57(s, OCH$_3$), 73.14(s, —C—) 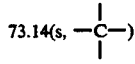

EXAMPLE 8

Synthesis of 2-propoxyisobutylbromide

N-Bromosuccinimide (3.56, 0.02 mol) was dissolved in 1-propanol. The product was obtained by procedures analogous to those described in Example 1 (93% yield).

IR(neat/$\nu$ cm$^{-1}$) 2980, 2945, 2880, 1465, 1430, 1380, 1370, 1100, 1080, 675.

$^1$HNMR(200MHz, CDCl$_3$/$\delta$ ppm): 0.91(t, 3H, CH$_3$), 1.29(s,6H,2CH$_3$), 1.54(m, 2H, CH$_2$), 3.27(t,2H,OCH$_2$), 3.39(s, 2H, CH$_2$Br).

$^{13}$CNMR(200MHz, CDCl$_3$/$\delta$ ppm): 10.84(s,CH$_3$), 23.72(s,CH$_2$), 24.52(s,2CH$_3$), 41.47(s,CH$_2$Br), 63.76(s,OCH$_2$), 73.48(s, —C—) 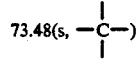

EXAMPLE 9

Synthesis of 2-isopropoxyisobutylbromide

N-Bromosuccinimide(3.56 g, 0.02 mol) was dissolved in 2-propanol. The product was obtained by procedures analogous to those described in Example 1 (93% yield).

IR(neat/$\nu$ cm$^{-1}$) 2980, 2955, 2880, 1470, 1430, 1380, 1370, 1120, 670.

$^1$HNMR(200MHz, CDCl$_3$/$\delta$ ppm):

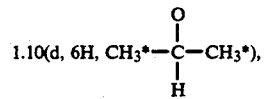

1.10(d, 6H, CH$_3$*—C—CH$_3$*),

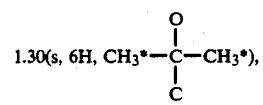

1.30(s, 6H, CH$_3$*—C—CH$_3$*), 3.35(s, 2H, CH$_2$), 3.79(m, 1H, CH)

$^{13}$CNMR(200MHz, CDCl$_3$/$\delta$ ppm): 25.10 and 25.17(s,CH$_3$), 42.21(s,CH$_2$), 64.65(s,OCH), 74.55(s, —C—) 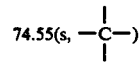

EXAMPLE 10

Synthesis of 2-propoxyisobutylisonitrile

The product was obtained by procedures analogous to those described in Example 4 (55% yield).

IR(neat/$\nu$ cm$^{-1}$) 2980, 2950, 2880, 2160, 1470, 1380, 1370, 1120, 1080.

$^1$HNMR(200MHz, CDCl$_3$/$\delta$ ppm): 0.92(t,3H,CH$_3$), 1.28(s,6H,2CH$_3$), 1.57(m,2H,CH$_2$), 3.28(m,2H,OCH$_2$), 3.36(t,2H,CH$_2$—N≡C).

$^{13}$CNMR(200MHz, CDCl$_3$/$\delta$ ppm): 10.79(s,CH$_3$), 23.21(s,2CH$_3$), 23.64(s,CH$_2$), 50.97(t,CH$_2$-N), 63.86(s,OCH$_2$), 73.01(s, —C—) 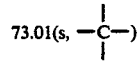

EXAMPLE 11

Preparation of tetrakis(2-methoxyisobutylisonitrile) copper(I) tetrafluoroborate Tetrakis(acetonitrile)copper(I)tetrafluoroborate(0.50 g, $1.6\times10^{-3}$ mol) was suspended in 100 ml of ethanol. 2-Methoxyisobutylisonitrile (0.72 g, $6.4\times10^{-3}$ mol) was slowly added and stirred at room temperature for an hour. The solvent was then evaporated completely under reduced pressure. The product was recrystallized from ethanol/ether (0.91 g, 95% yield), M.P. 100°–101° C. Anal. Calcd. for $C_{24}H_{44}N_4O_4CuBF_4$: C,47.80;H,7.30; N,9.29: Cu,10.54; B,1.79; F,12.62. Found: C,47.69: H,7.40: N,9.05: Cu,10.52; B,1.80; F,12.71.

IR(Nujol mull/$\nu$ cm$^{-1}$): 2200

$^1$HNMR(200MHz, CDCl$_3$/$\delta$ ppm): 1.29(s,6H,2CH$_3$), 3.25(s,3H,OCH$_3$), 3.61(s,2H,CH$_2$)

$^{13}$CNMR(200MHz,CDCl$_3$/$\delta$ ppm): 22.60(s,2CH$_3$), 50.09(s,OCH$_3$), 51.72(d,CH$_2$),

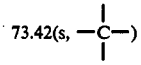

EXAMPLE 12

Preparation of tetrakis(2-ethoxyisobutylisonitrile)copper(I) tetrafluoroborate To a stirred suspension of tetrakis(acetonitrile)copper(I) tetrafluoroborate(0.50 g, $1.6\times10^{-3}$ mol) in 100 ml of ethanol at room temperature, was slowly added 2-ethoxyisobutylisonitrile (0.81 g, $6.4\times10^{-3}$ mol). After the reaction mixture was stirred for 30 minutes to give a clear solution, the solvent was then evaporated to dryness under reduced pressure. The product was recrystallized from ethanol/n-hexane, and the white solids obtained were washed with n-hexane and dried in vacuo: (1.01 g, 96% yield), M.P. 76°–77° C. Anal. Calcd for $C_{28}H_{52}N_4O_4CuBF_4$: C,51.04: H,7.90; N,8.51; Cu,9.65: B,1.64: F,11.54. Found: C,51.10; H,7.85; N,8.59; Cu,9.61: B,1.70; F,11.61.

IR(Nujol mull/$\nu$ cm$^{-1}$): 2200

$^1$HNMR(200MHz, CDCl$_3$/$\delta$ ppm): 1.18(t,3H,CH$_3$), 1.29(s,6H,2CH$_3$), 3.43(q,2H,OCH$_2$),3.59(s,2H,CH$_2$)

$^{13}$CNMR(200MHz, CDCl$_3$/$\delta$ ppm): 16.06(s,CH$_3$), 23.38(s,2CH$_3$), 52.03(s,CH$_2$), 57.66(s,OCH$_2$),

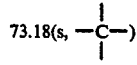

EXAMPLE 13

Preparation of Tc-99m-alkoxyisobutylisonitrile complexes

In a 8 ml-vial are mixed tetrakis(2-methoxyisobutylisonitrile) copper(I)tetrafluoroborate(1–2mg) or tetrakis(2-ethoxyisobutylisonitrile)copper(I)tetrafluoroborate (1–2 mg), sodium citrate dihydrate(2.2–3.2 mg), mannitol(16–26 mg), cysteine hydrochloride(1–3 mg) and stannous chloride(0.05–0.09 mg). The vials were sealed and 25–40 mCi(1–2 ml) $^{99m}$TcO$_4^-$ obtained by elution of a $^{99}$Mo/$^{99m}$Tc radionuclide generator was added. The vials were heated in a 95°–100° C. water bath for 10–15 min. and allowed to cool to room temperature. Quality assurance of in vitro stability was done on ITLC(SG) with saline and methylethylketone(-MEK) to determine $^{99m}$TcO$_2$(Rf:0), $^{99m}$TcO$_4^-$(Rf:0-.9–1.0) and the $^{99m}$Tc isonitrile complex (MEK:Rf:MMI 0.45, EMI 0.8; saline:0).

We claim:

1. A method for synthesis of 2-alkoxyisobutylisonitrile using isobutylene as the starting material, said method comprising a haloalkoxylation of said isobutylene to give 2-alkoxyisobutylhalide, converting the 2-alkoxyisobutylhalide to 2-alkoxyisobutylamine, and under basic conditions reacting said 2-alkoxyisobutylamine with chloroform to produce 2-alkoxyisobutylisonitrile, wherein the product 2-alkoxyisobutylisonitrile has a general formula

wherein R is an alkyl group having 1–4 carbon atoms.

2. The method of claim 1 wherein said 2-alkoxyisobutylhalide is synthesized by reacting isobutylene with N-halosuccinimide at temperature of $-50°$–$0°$ C. in alcohol solvent.

3. The method of claim 1 wherein said 2-alkoxyisobutylamine is synthesized by reacting 2-alkoxyisobutylhalide with potassium phthalimide and hydrazine at temperature of 100°–200° C.

4. The method of claim 1 wherein said 2-alkoxyisobutylisonitrile is synthesized by reacting 2-alkoxyisobutylamine with chloroform, sodium hydroxide and catalyst benzyltriethylammonium chloride at 50°–100° C. temperature.

5. The method of claim 1, wherein the 2-alkoxyisobutylisonitrile is 2-methoxyisobutylisonitrile.

6. The method of claim 1, wherein the 2-alkoxyisobutylisonitrile is 2-ethoxyisobutylisonitrile.

7. The method of claim 1, wherein the 2-alkoxyisobutylisonitrile is 2-propoxyisobutylisonitrile.

* * * * *